United States Patent [19]

Smith

[11] 4,147,879

[45] Apr. 3, 1979

[54] 2,2-DIFLUORO-13,14 DIDEHYDRO-PGF$_1$ COMPOUNDS

[75] Inventor: Herman W. Smith, Kalamazoo, Mich.

[73] Assignee: The Upjohn Company, kalamazoo, Mich.

[21] Appl. No.: 776,551

[22] Filed: Mar. 7, 1977

Related U.S. Application Data

[62] Division of Ser. No. 657,739, Feb. 13, 1976, Pat. No. 4,029,681.

[51] Int. Cl.$^2$ ............................................. C07C 177/00
[52] U.S. Cl. .................................... 560/121; 260/408; 562/503
[58] Field of Search ........................ 560/121; 562/503; 260/408

[56] References Cited

PUBLICATIONS

Medicinal Chemistry, 2nd ed. pp. 81–83 (1960).

*Primary Examiner*—Robert Gerstl
*Attorney, Agent, or Firm*—Robert A. Armitage

[57] ABSTRACT

This invention comprises certain analogs of the prostaglandins in which the double bond between C-13 and C-14 is replaced by a triple bond. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

67 Claims, No Drawings

2,2-DIFLUORO-13,14 DIDEHYDRO-PGF₁ COMPOUNDS

The present application is a divisional application of Ser. No. 657,739, filed Feb. 13, 1976, now U.S. Pat. No. 4,029,681.

The present invention relates to prostaglandin analogs, for which the essential material constituting disclosure therefor is incorporated by reference here from Ser. No. 657,739, filed Feb. 13, 1976, now pending issuance as a United States Patent.

I claim:

1. A prostaglandin analog of the formula:

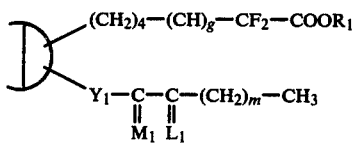

wherein D is

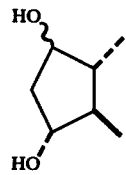

or

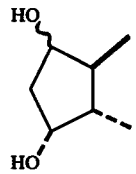

wherein $Y_1$ is —C≡C—;
wherein g is one, two, or 3;
wherein m is one to 5, inclusive;
wherein $M_1$ is

or

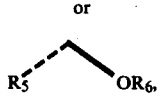

wherein $R_5$ and $R_6$ are hydrogen or methyl, with the proviso that one of $R_5$ and $R_6$ is methyl only when the other is hydrogen;
wherein $L_1$ is

or a mixture of

and

wherein $R_3$ and $R_4$ are hydrogen, methyl, or fluoro, being the same or different, with the proviso that one of $R_3$ and $R_4$ is fluoro only when the other is hydrogen or fluoro;
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein D is

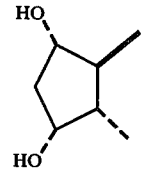

3. A compound according to claim 2, wherein $M_1$ is

4. A compound according to claim 3, wherein g is one.

5. A compound according to claim 4, wherein $R_3$, $R_4$, $R_5$, and $R_6$ are all hydrogen.

6. A compound according to claim 2, wherein $M_1$ is

7. A compound according to claim 6, wherein g is three.

8. A compound according to claim 6, wherein g is one.

9. A compound according to claim 8, wherein $R_3$ and $R_4$ are both hydrogen.

10. A compound according to claim 9, wherein $R_5$ is methyl.

11. A compound according to claim 9, wherein $R_6$ is methyl.

12. 2,2-Difluoro-13,14-didehydro-8β,12α-PGF₁α, 15-methyl ether, a compound according to claim 11.

13. 2,2-Difluoro-13,14 -didehydro-8β,12α-PGF₁α, methyl ester, 15-methyl ether, a compound according to claim 11.

14. A compound according to claim 9, wherein $R_5$ and $R_6$ are both hydrogen.

15. 2,2-Difluoro-13,14-didehydro-8β,12α-PGF₁α, a compound according to claim 14.

16. 2,2-Difluoro-13,14-didehydro-8β,12α-PGF₁α, methyl ester, a compound according to claim 14.

17. A compound according to claim 8, wherein at least one of $R_3$ and $R_4$ is methyl.

18. A compound according to claim 17, wherein $R_3$ and $R_4$ are both methyl.

19. A compound according to claim 18, wherein $R_5$ is methyl.

20. 2,2-Difluoro-15,16,16-trimethyl-13,14-didehydro-8β,12α-PGF$_1$α, methyl ester, a compound according to claim 19.

21. A compound according to claim 18, wherein R$_6$ is methyl.

22. 2,2-Difluoro-16,16-dimethyl-13,14-didehydro-8β,12α-PGF$_1$α, methyl ester, 15-methyl ether, a compound according to claim 21.

23. A compound according to claim 18, wherein R$_5$ and R$_6$ are both hydrogen.

24. 2,2-Difluoro-16,16-dimethyl-13,14-didehydro-8β,12α-PGF$_1$α, a compound according to claim 23.

25. 2,2-Difluoro-16,16-dimethyl-13,14-didehydro-8β,12α-PGF$_1$α, methyl ester, a compound according to claim 23.

26. A compound according to claim 8, wherein at least one of R$_3$ and R$_4$ is fluoro.

27. A compound according to claim 26, wherein R$_3$ and R$_4$ are both fluoro.

28. A compound according to claim 27, wherein R$_5$ is methyl.

29. 2,2-Difluoro-15-methyl-16,16-difluoro-13,14-didehydro-8β,12α-PGF$_1$α, methyl ester, a compound according to claim 28.

30. A compound according to claim 27, wherein R$_6$ is methyl.

31. 2,2-Difluoro-16,16-difluoro-13,14-didehydro-8β,12α-PGF$_1$α, methyl ester, 15-methyl ether, a compound according to claim 30.

32. A compound according to claim 27, wherein R$_5$ and R$_6$ are both hydrogen.

33. 2,2-Difluoro-16,16-difluoro-13,14-didehydro-8β,12α-PGF$_1$α, a compound according to claim 32.

34. 2,2-Difluoro-16,16-difluoro-13,14-didehydro-8β,12α-PGF$_1$α, methyl ester, a compound according to claim 32.

35. A compound according to claim 1, wherein D is

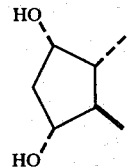

36. A compound according to claim 35, wherein M$_1$ is

37. A compound according to claim 36, wherein g is one.

38. A compound according to claim 37, wherein R$_3$, R$_4$, R$_5$, and R$_6$ are all hydrogen.

39. A compound according to claim 35, wherein M$_1$ is

40. A compound according to claim 39, wherein g is three.

41. A compound according to claim 39, wherein g is one.

42. A compound according to claim 41, wherein R$_3$ and R$_4$ are both hydrogen.

43. A compound according to claim 42, wherein R$_5$ is methyl.

44. A compound according to claim 42, wherein R$_6$ is methyl.

45. 2,2-Difluoro-13,14-didehydro-PGF$_1$α, 15-methyl ether, a compound according to claim 44.

46. 2,2-Difluoro-13,14-didehydro-PGF$_1$α, methyl ester, 15-methyl ether, a compound according to claim 44.

47. A compound according to claim 42, wherein R$_5$ and R$_6$ are both hydrogen.

48. 2,2-Difluoro-13,14-didehydro-PGF$_1$α, a compound according to claim 47.

49. 2,2-Difluoro-13,14-didehydro-PGF$_1$α, methyl ester, a compound according to claim 47.

50. A compound according to claim 41, wherein at least one of R$_3$ and R$_4$ is methyl.

51. A compound according to claim 50, wherein R$_3$ and R$_4$ are both methyl.

52. A compound according to claim 51, wherein R$_5$ is methyl.

53. 2,2-Difluoro-15,16,16-trimethyl-13,14-didehydro-PGF$_1$α, methyl ester, a compound according to claim 52.

54. A compound according to claim 51, wherein R$_6$ is methyl.

55. 2,2-Difluoro-16,16-dimethyl-13,14-didehydro-PGF$_1$α, methyl ester, 15-methyl ether, a compound according to claim 54.

56. A compound according to claim 51, wherein R$_5$ and R$_6$ are both hydrogen.

57. 2,2-Difluoro-16,16-dimethyl-13,14-didehydro-PGF$_1$α, a compound according to claim 56.

58. 2,2-Difluoro-16,16-dimethyl-13,14-didehydro-PGF$_1$α, methyl ester, a compound according to claim 56.

59. A compound according to claim 41, wherein at least one of R$_3$ and R$_4$ is fluoro.

60. A compound according to claim 59, wherein R$_3$ and R$_4$ are both fluoro.

61. A compound according to claim 60, wherein R$_5$ is methyl.

62. 2,2-Difluoro-15-methyl-16,16-difluoro-13,14-didehydro-PGF$_1$α, methyl ester, a compound according to claim 61.

63. A compound according to claim 60, wherein R$_6$ is methyl.

64. 2,2-Difluoro-16,16-difluoro-13,14-didehydro-PGF$_1$α, methyl ester, 15-methyl ether, a compound according to claim 63.

65. A compound according to claim 60, wherein R$_5$ and R$_6$ are both hydrogen.

66. 2,2-Difluoro-16,16-difluoro-13,14-didehydro-PGF$_1$α, a compound according to claim 65.

67. 2,2-Difluoro-16,16-difluoro-13,14-didehydro-PGF$_1$α, methyl ester, a compound according to claim 65.

* * * * *

UNITED STATES PATENT OFFICE
CERTIFICATE OF CORRECTION

Patent No. 4,147,879            Dated April 3, 1979

Inventor(s) Herman W. Smith

It is certified that error appears in the above-identified patent and that said Letters Patent are hereby corrected as shown below:

Column 1, lines 11-12, "Ser. No. 657,739, filed Feb. 13, 1976, now pending issuance as a United States Patent." should read -- United States Patent 4,029,681, issued June 14, 1977. --

Signed and Sealed this

*Eleventh* Day of *September 1979*

[SEAL]

Attest:

LUTRELLE F. PARKER
*Attesting Officer*      *Acting Commissioner of Patents and Trademarks*